United States Patent

Ueda

[11] 4,181,122
[45] Jan. 1, 1980

[54] DEVICE FOR MEASURING BLOOD PRESSURE

[75] Inventor: Kazuo Ueda, Tokyo, Japan

[73] Assignee: Ueda Works Co., Ltd., Tokyo, Japan

[21] Appl. No.: 787,638

[22] Filed: Apr. 14, 1977

Related U.S. Application Data

[63] Continuation-in-part of Ser. No. 601,572, Aug. 1, 1975, abandoned.

[51] Int. Cl.$^2$ .................................................. A61B 5/02
[52] U.S. Cl. ................................. 128/680; 179/1 ST; 181/171
[58] Field of Search ............... 128/2.05 A, 2.05 G, 128/2.05 M, 2.05 S, 2 K; 179/1 ST; 181/126, 131, 137, 158, 171, 172

[56] References Cited

U.S. PATENT DOCUMENTS

| | | | |
|---|---|---|---|
| 2,865,395 | 12/1958 | Newland et al. | 128/2.05 A |
| 2,946,645 | 7/1960 | Schwarzer | 128/2.05 S X |
| 3,101,082 | 8/1963 | Steen et al. | 128/2.05 M |
| 3,104,661 | 9/1963 | Halpern | 128/2.05 A |
| 3,117,570 | 1/1964 | Halasz et al. | 128/2.05 M |
| 3,450,131 | 6/1969 | Vogt | 128/2.05 A |
| 3,480,004 | 11/1969 | Edwards | 128/2.05 M |
| 3,555,187 | 1/1971 | Rowley | 179/1 ST |
| 3,573,394 | 4/1971 | Birnbaum | 128/2.05 S |
| 3,623,478 | 11/1971 | Saba | 128/2.05 M X |
| 3,868,954 | 3/1975 | Ueda | 128/2.05 S |
| 3,930,494 | 1/1976 | Maurer et al. | 128/2.05 A |
| 4,012,604 | 3/1977 | Speidel | 128/2.05 S X |

*Primary Examiner*—Lee S. Cohen
*Attorney, Agent, or Firm*—Kane, Dalsimer, Kane, Sullivan & Kurucz

[57] ABSTRACT

Device for use in measurement of blood pressure, according to the intermediate blood pressure measuring method of RIVA ROCCI, which detects negative signals of Korotkoff sound pulses comprised in asymmetrical alternating current signal waves coming from a ceramic microphone through a band pass filter and a half-wave rectifier, and indicates the presence of the Korotkoff sound after shaping the negative signals in a monostable multivibrator.

1 Claim, 3 Drawing Figures

DEVICE FOR MEASURING BLOOD PRESSURE

This application is a Continuation-in-part of my co-pending U.S. patent application Ser. No. 601,572 filed Aug. 1, 1975, now abandoned.

BACKGROUND OF THE INVENTION

1. Field of the Invention

The present invention relates to improvements in a device, for use in measuring blood pressure according to the intermediate blood pressure measuring method of RIVA ROCCI, which comprises for example a ceramic microphone, a combination of an air compressing means, and means for securing said ceramic microphone to an arm of the person whose blood pressure is to be measured, and other electronic device.

2. The Prior Art

Conventionally, in such a device for use in measuring blood pressure by detecting the Korotkoff sound in the blood circulation by means of a microphone, it is a troublesome problem to eliminate extraneous noises of various kinds entering the detecting devices. It is especially difficult to eliminate a pressure pulse which coexists with said Korotkoff sound, and many devices and methods for eliminating said pressure pulse have been proposed. In the prior art devices attempts have been made to discriminate Korotkoff sound and said pressure noise, for eliminating the latter, by utilizing a difference in frequency between them, and a device has been provided comprising appropriate filter circuits to discriminate and eliminate the pressure pulse, and to lower the crest value (peak value) of the wave form of the pressure pulse from that of the Korotkoff sound, and means for eliminating the pressure pulse by determining a suitable threshold level.

However, there have not so far been proposed any effective methods or devices for eliminating the pressure pulse from the Korotkoff sound. The reason is that among the Korotkoff sound and the other various sounds (noises, including the pressure pulse above-mentioned) there are conspicuous individual differences which greatly influence the results obtained.

SUMMARY OF OBJECTS OF THE INVENTION

A first object of the present invention is to provide a device for use in measuring blood pressure which comprises a ceramic microphone, a combination of an air compressing means and means for securing said microphone to an arm of the person whose blood pressure is to be measured, and other electronic circuits, and which can discriminate the pressure pulse from the Korotkoff sound so as to be able to detect only the negative signal of said Korotkoff sound by utilizing the difference between the signal wave forms of said Korotkoff sound and said pressure pulse.

A second object of the present invention is to provide a compact device for use in measuring blood pressure.

DETAILED DESCRIPTION OF THE INVENTION

The present invention will now be described in conjunction with the accompanying drawings.

Figure 1:
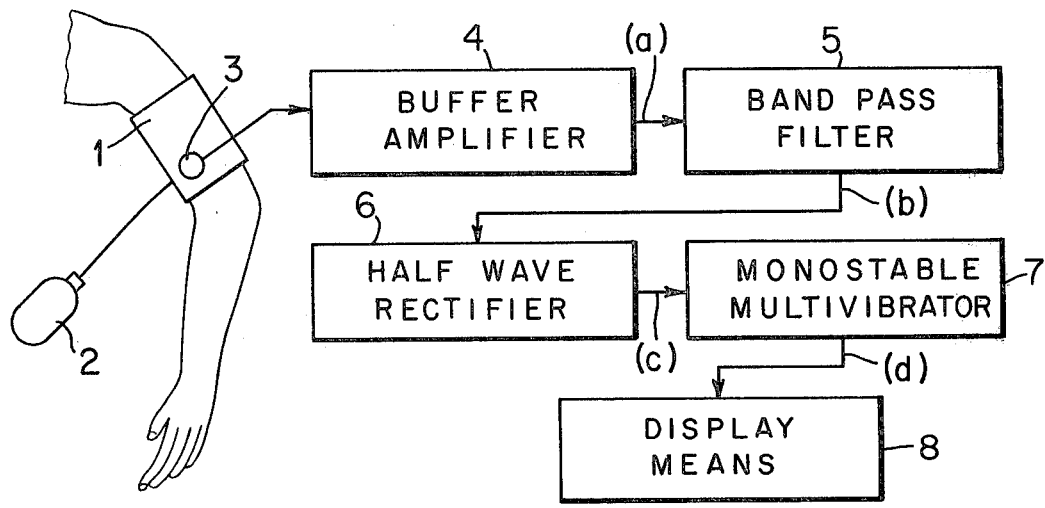
FIG. 1 is a block diagram illustrating one embodiment of the present invention.

Referring to FIG. 1, reference number 1 is a wrapping cloth for fixing the device for use in measuring blood pressure to an arm of a person whose blood pressure is to be measured, 2 designates an air supply device (small air compressor having a rubber bulb, or a pump) for adjusting exterior pressure in the device, and 3 is a ceramic piezo-electric microphone to be described in greater detail hereinafter.

4 is a buffer amplifier which amplifies asymmetrical alternating current signals coming from said microphone 3. 5 is a band pass filter which eliminates both high frequency noises and very low frequency noises, and it is used for wave form shaping (to confine the filtered wave form to a fundamental frequency band of the genuine (Korotkoff sound) pulse form). 6 is a half wave rectifier (rectifying circuit) which selects the negative side of the wave form of the signal coming from said filter 5. 7 is a monostable multivibrator for shaping the signals transmitted from the half wave rectifier 6, and 8 is an indicator means such as a buzzer or a light emitting diode which functions with the signals from the monostable multivibrator 7 and gives indications which either a measurer, or the person being measured, or both, can perceive.

Figure 3:
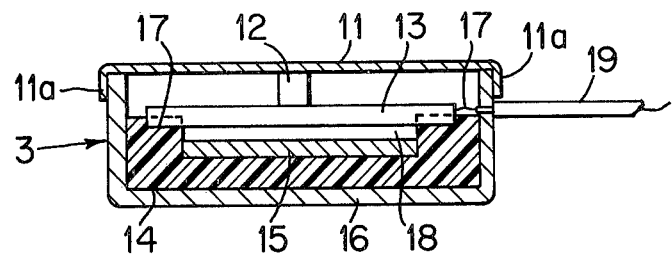
FIG. 3 is a sectional view of a ceramic microphone of the present invention.

Referring to FIG. 3, description is now made in greater detail of the ceramic microphone 3. The ceramic microphone 3 is an improvement in the microphone invented by the inventor of the present invention for the purposes of improving pressure sensitivity of a hemadynamometer microphone so as to be able to respond to diaphragm oscillations and also for improving its physical resistance to heat and shocks, and the prior ceramic microphone was patented under U.S. Pat. No. 3,868,954.

Reference numeral 16 designates a microphone housing. Reference numeral 11 designates an oscillatable diaphragm mounted on the microphone housing 16 with its flange 11a in contact with the outer periphery of the housing 16. The flange 11a of the diaphragm 11 is provided to reinforce the mechanical strength of the diaphragm 11, and serves to prevent excessive strains in the housing 16. Reference 13 designates a ceramic element utilized as a transducer for converting sounds into electric oscillations. Unlike the usual piezo-electric crystal element, it is strongly heat-resistant and has good oscillating performance. On the other hand, the ceramic element is very fragile. This drawback is effectively overcome by the following construction utilizing a resilient relay member 12 and a resilient support member 14. The resilient relay member 12 is made of resilient material such as sponge, rubber or the like.

It has been experimentally found that Neoprene rubber with a hardness of 50 is most suitable as the resilient material for them. These resilient rubber members also absorb external shocks and thus protect the physically fragile ceramic element 13 supported between them. The resilient relay member 12 between the oscillating diaphragm 11 and the ceramic element 13 transmits the oscillation of the oscillating diaphragm 11 to the ceramic element 13. The resilient support member 14 supports the ceramic member 13 within the microphone housing 16. The resilient support member 14 has its lower portion snugly fitted into the lower part of the cap 16. With the above construction of the microphone 3, the ceramic element 13 can be readily positioned in the center of the cap 16 to greatly simplify the assembly. Further, because the support member 14 consists of only a single part, rather than two parts as in the prior art, the number of parts can be reduced, so that the assembly can further be facilitated, while nevertheless ensuring reliable positioning.

Support member 14 is formed with support grooves 17 for supporting the opposed ends of the ceramic element 13. The resilient support member 14 is characterized by its configuration; it consists of a centrally recessed elongate body comprising a pair of upwardly and inwardly opening grooves 17, 17 longitudinally and symmetrically formed near the ends thereof, so that the ceramic element 13 may easily be supported on the support member 14 with its opposite ends fitted in the grooves and its major central portion spaced from the support member 14.

Numeral 19 designates a microphone cord electrically connected to the ceramic element 13. The coupling of the above parts, for instance the coupling between microphone housing 16 and resilient support member 14, and the coupling between the microphone housing 16 and the oscillating diaphragm 11, are all obtained by means of bonding. A typical example of the method of assembly consists of mounting the resilient support member 14 in the microphone housing 16, mounting the ceramic element 13 in the support member 14, soldering the element 13 to the microphone cord 19, bonding the relay element 12 to the ceramic element 13, and mounting the oscillating diaphragm 11 on the microphone cap 16 with the diaphragm bonded to the microphone cap 16 and to the relay member 12 in the abovementioned order.

Under such a structure of the microphone of U.S. Pat. No. 3,868,954, in accordance with the improvement of the present invention, in the lower part of the recess 18 of the resilient support member 14 a support plate 15 made of metal or other rigid material is secured by adhesive. Thus, even if the microphone 3 should be inadvertently dropped, or any strong blows administered to it, distortion caused by the shock on the resilient supporting member 14 is completely prevented within predetermined limits by said support plate 15.

The use of the device in measuring the blood pressure is described hereinbelow.

As is well known, using a wrapping cloth 1 and the air compressor 2, the output of the ceramic microphone 3 is electrical signals which are transmitted to the buffer amplifier 4.

The buffer amplifier 4 amplifies said electrical signals.

Figure 2:
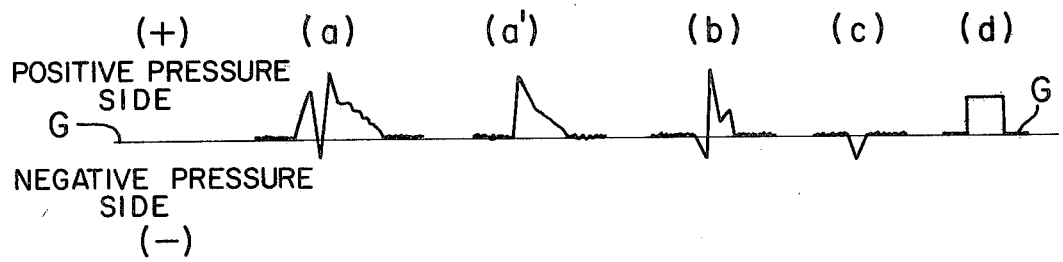
FIG. 2 shows wave shapes illustrating features of the present invention.

As shown in graph (a) in FIG. 2, the amplified signal output from the buffer amplifier 4 (i.e. the output signal of the ceramic microphone 3) is an asymmetrical alternating current signal including positive and negative signals of Korotkoff sound as well as positive pressure pulses and other noises with respect to the base line G. Here, the positive signal means a signal appearing on the positive pressure side (+) (i.e. the upper side from the base line G); similarly, a negative signal means a signal appearing on the negative pressure side (−) (i.e. the lower side from the base line G.)

The graph (a') in FIG. 2 shows the wave form of the pressure pulse.

The present invention shows remarkable differences between the wave forms (a) and (a') shown in FIG. 2 obtained and ascertained by the experiment. The essence of the present invention lies in the improvement of the device for use in measuring blood pressure, based on the intermediate blood pressure measuring method of RIVA ROCCI, by which the present inventor has succeeded in eliminating various kinds of noises such as the pressure pulse, and selecting only the Korotkoff sound by a ceramic microphone 3 and other electronic means.

The fact that the wave form of the output signal detected by the ceramic microphone 3 is as shown in FIG. 2(a), and that the wave form of the pressure pulse which is the most troublesome obstacle for selecting Korotkoff sound from the output signal is as shown in FIG. 2(a'), can be ascertained by experiment.

As will be apparent from a comparison of said wave forms (a) and (a') in FIG. 2, in the wave forms of the sounds comprising Korotkoff sound and other various sounds (noises) shown in graph (a) in FIG. 2, there are amplitude variations on both the positive and the negative pressure sides (i.e., upper and lower pressure sides with respect to the base line G) of the base line G of the graph. However, in graph (a') showing the wave form of the pressure pulse there is scarcely any amplitude variation in the negative pressure side of the graph, and scarcely any differences can be recognized among individuals.

In view of this, the present inventor devised the compact electronical device for use in measuring blood pressure capable of obtaining exact measuring value of sound composed almost only of Korotkoff sound, by selecting wave forms in which scarcely any individual differences can be seen.

After passing through the band pass filter 5, the high frequencies and the very low frequencies are filtered, and only the fundamental frequency band of the genuine pulse is selected.

Thus, the wave form shown as graph (b) in FIG. 2 is obtained.

Then, by passing through the half wave rectifier 6, the positive signal of the Korotkoff sound as well as that of the pressure pulse and the other various noises are removed, and only the negative side of the wave form of the signal coming from said filter 5 is selected. This appears as graph (c) in FIG. 2. It is apparent from the graph there cannot be seen any signal of the pressure pulse and other noises in the graph. The wave form shown as graph (d) is the rectangular wave form of the signal filtered by the half wave filtering circuit 6 and shaped by the monostable multivibrator 7. The rectangular wave form (d) is then transferred to the display means 8, such as a buzzer or a light-emitting diode.

Blood pressure measurements on 200 persons have been carried out by employing both the present device and a stethoscope and sphygmomanometer at the same time, and the results of the measurements verify that the present device has very excellent precision when used in method of measuring blood pressure, that is, there are scarcely a little difference between the values measured by these two devices. For example, in the mean values of maximum of blood pressure, they differ only by 0.6, and in the standard deviation values there are differences of only 4.8 between them. Further, in the mean values of the minimum of blood pressure there are only differences of 0.06, and in the standard deviation values between them they differ from each other only by 3.2.

It is found that the most effective microphone used in the present invention is a ceramic type of which the frequency characteristic curve is as follows; in the frequency range from 100 Hertz to 10K Hertz the frequency characteristic should be nearly flat, and at other frequency ranges (higher than 10K Hertz and lower than 100 Hertz) it should attenuate 6dB/Octave.

With the present device, for use in measuring blood pressure, only the negative signal of the Korotkoff sound can be effectively selected from those sounds detected by the ceramic microphone 3, so that measurement of blood pressure can be easily and precisely performed.

Further, the present invention permits the making of a compact device for use in blood pressure measuring which can give precise blood pressure readings at low cost.

I claim:

1. A device, for indicating the presence and absence of Korotkoff sound in the measurement of intermediate blood pressure measuring according to RIVA ROCCI, comprising:
   (i) a microphone composed of
      (a) a housing having an opening;
      (b) a support member of resilient material in said housing, said support member being an elongated single-piece body having a central recess and first and second longitudinal grooves formed symmetrically adjacent the respective ends of the body and opening upwardly and inwardly therein, said support member fitting snugly within said housing, in the lower part of said recess of said support member a support plate made of rigid material being secured by adhesive;
      (c) a ceramic element positioned within said housing and having its ends engaged in said first and second grooves and with a major central part thereof intermediate said ends overlying said recess so as to be in spaced relationship from said support member;
      (d) a diaphragm secured on said housing over the opening thereof, and a connecting element made of resilient material and disposed centrally of said ceramic element and positioned between and connected to said ceramic element and said diaphragm for transmission of vibrations of said diaphragm to said ceramic element;
   (ii) a buffer amplifier electrically connected to said microphone for amplifying asymmetrical alternating current signals emitted by the microphone;
   (iii) a bandpass filter electrically connected to the amplifier for passing only a frequency band of the output signal of the amplifier, by elimination of high frequency noise and very low frequency noise, such that said band substantially includes only the fundamental frequency of the Korotkoff sound signal;
   (iv) a half-wave rectifier electrically connected to the bandpass filter for removing, from the passband signal, the positive pressure portions of the waveform of the signal coming from said filter, thereby to provide a negative signal corresponding only to the Korotkoff sound;
   (v) a monostable multivibrator electrically connected to the half-wave rectifier for shaping said negative-pressure signal; and
   (vi) indicating means electrically connected to the monostable multivibrator for indicating the shaped negative-pressure signal.

* * * * *